(12) United States Patent
Smith

(10) Patent No.: US 9,441,807 B2
(45) Date of Patent: Sep. 13, 2016

(54) RESIN-BASED SCULPTURES WITH AESTHETICALLY PLEASING HARDWARE

(71) Applicant: 3form, Inc., Salt Lake City, UT (US)

(72) Inventor: Ryan Grey Smith, Seattle, WA (US)

(73) Assignee: 3Form, LLC, Salt Lake City, UT (US)

( * ) Notice: Subject to any disclaimer, the term of this patent is extended or adjusted under 35 U.S.C. 154(b) by 436 days.

(21) Appl. No.: 13/787,455

(22) Filed: Mar. 6, 2013

(65) Prior Publication Data

US 2013/0235591 A1 Sep. 12, 2013

Related U.S. Application Data

(60) Provisional application No. 61/608,093, filed on Mar. 7, 2012.

(51) Int. Cl.

| | |
|---|---|
| *F21V 3/00* | (2015.01) |
| *F21V 1/22* | (2006.01) |
| *F21V 1/26* | (2006.01) |
| *F21S 8/06* | (2006.01) |
| *F21Y 101/02* | (2006.01) |
| *A61F 13/26* | (2006.01) |

(52) U.S. Cl.
CPC . *F21V 1/22* (2013.01); *F21V 1/26* (2013.01); *A61F 13/266* (2013.01); *F21S 8/061* (2013.01); *F21Y 2101/02* (2013.01); *Y10T 29/4998* (2015.01); *Y10T 428/24479* (2015.01)

(58) Field of Classification Search
CPC ............................ F21S 8/061; F21Y 2101/02
USPC ..................................................... 362/311.04
See application file for complete search history.

(56) References Cited

U.S. PATENT DOCUMENTS

| | | | | |
|---|---|---|---|---|
| 103,928 | A * | 6/1870 | Read, Jr. ...................... | 362/360 |
| 3,433,939 | A * | 3/1969 | Lothman ...................... | 362/644 |
| 5,211,474 | A * | 5/1993 | Leitner et al. ................ | 362/351 |
| 7,504,159 | B1 * | 3/2009 | Suare et al. .................. | 428/532 |
| 2003/0081418 | A1 * | 5/2003 | Sviland ......................... | 362/356 |
| 2011/0089830 | A1 * | 4/2011 | Pickard et al. ................ | 315/32 |

* cited by examiner

*Primary Examiner* — Andrew Coughlin
*Assistant Examiner* — Meghan Ulanday
(74) *Attorney, Agent, or Firm* — Workman Nydegger

(57) ABSTRACT

The disclosure involves resin-based sculptures, such as resin-based lighting fixtures, that include resin pieces secured together by resin-based fasteners. One or more resin-based fasteners secure the resin pieces. Furthermore, the resin-based fasteners are configured to blend in with the resin pieces in a manner that reduces the visibility of the resin-based fasteners. For instance, the resin-based fasteners can have a color and/or shade that match the color and/or shade of the resin strips.

31 Claims, 10 Drawing Sheets

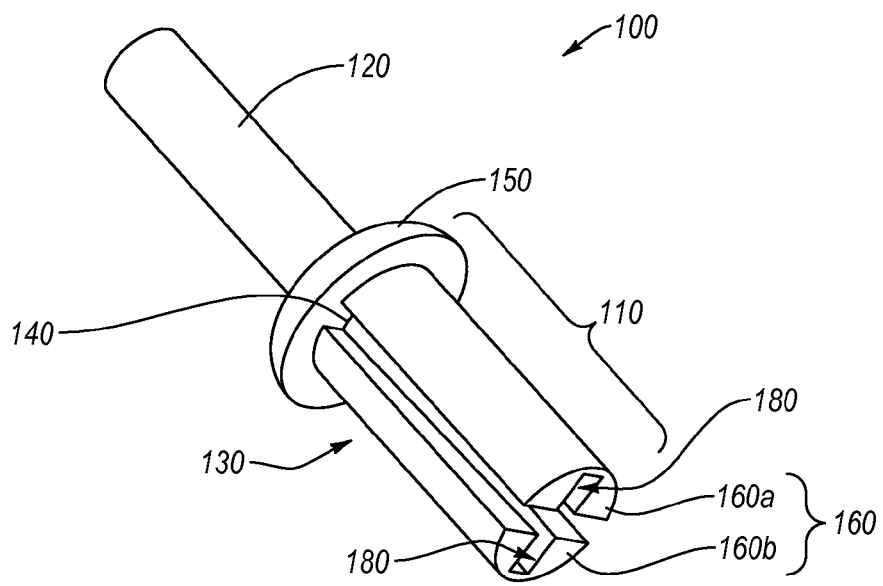
FIG. 1A
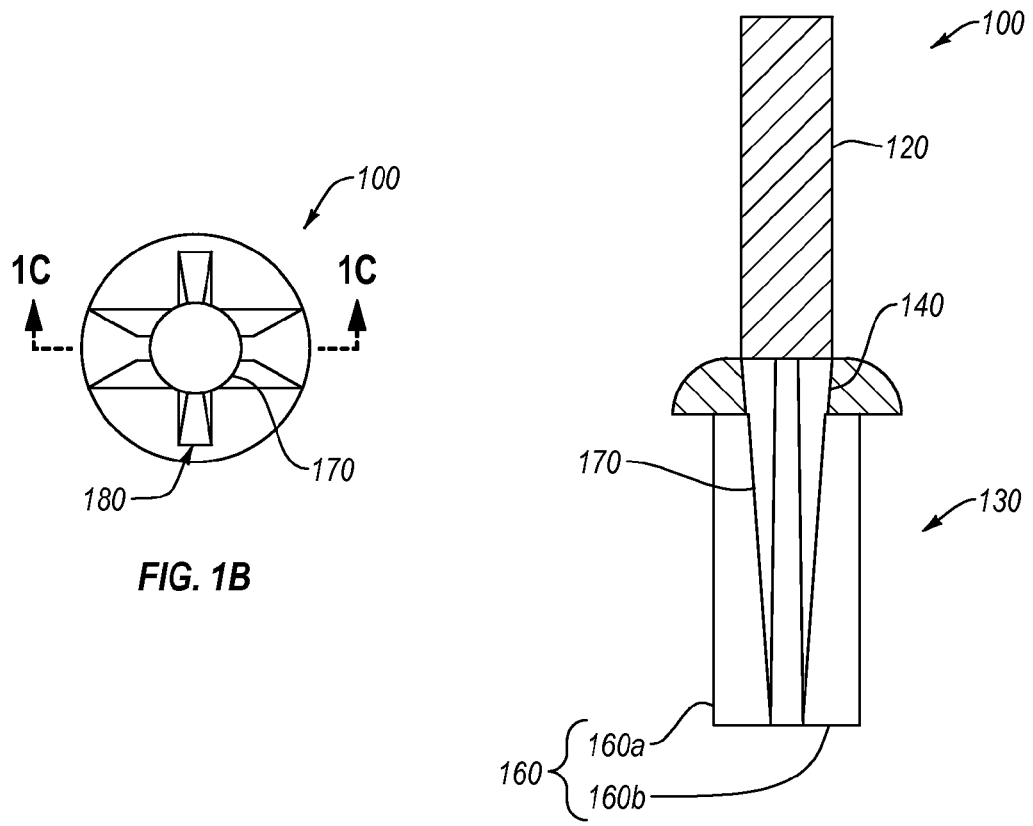
FIG. 1B
FIG. 1C

RESIN-BASED SCULPTURES WITH AESTHETICALLY PLEASING HARDWARE

CROSS-REFERENCE TO RELATED APPLICATIONS

The present application claims the benefit of priority to U.S. Provisional Patent Application No. 61/608,093, filed Mar. 7, 2012, entitled "Resin-Based Sculptures With Aesthetically Pleasing Hardware," the entire content of which is incorporated herein by this reference.

BACKGROUND

1. Technical Field

Implementations of the present invention relate to decorative resin-based sculptures and fasteners used for securing various portions of such sculptures.

2. Background and Relevant Art

Recent trends in building design involve using one or more sets of decorative panels to add to the functional and/or aesthetic characteristics of a given structure or design space. These recent trends are due, at least in part, because there is sometimes more flexibility with how the given panel (or set of panels) is designed, compared with the original structure. For example, recent panel materials include synthetic, polymeric resin materials, which can be formed as panels to be used as partitions, walls, barriers, treatments, décor, etc.

In particular, the use of resin materials is becoming increasingly popular in sculptural and lighting applications. In general, resin materials such as these are now popular compared with decorative cast or laminated glass materials, since resin materials may be manufactured to be more resilient and to have a similar transparent, translucent, or decorative appearance as cast or laminated glass, but with less cost. In addition, resin materials tend to be more flexible in terms of manufacture and assembly because they can be relatively easily bent, molded, colored, shaped, cut, and otherwise modified in a variety of different ways. Decorative resins can also provide more flexibility compared with glass and other conventional materials at least in terms of color, degree of texture, gauge, and impact resistance. Additionally, decorative resins have a fairly wide utility since they may be formed to include a large variety of colors, images, inter-layers, and shapes.

Unfortunately, some resin-based sculptures may require numerous hardware components and/or complicated hardware for assembly and installation procedures. Such hardware can be visible and unsightly. Indeed, mounting hardware of some conventional resin-based sculptures may be unappealing to designers and architects seeking to obtain a certain aesthetic by using resin-based products. For example, conventional metal hardware used to connect resin strips in many artistic resin-based sculptures can contrast with the resin and appear unsightly. The unappealing aesthetic of conventional hardware is often magnified when the resin-based sculpture is used as a lighting fixture. In particular, when such resin-based lighting fixtures are illuminated, the hardware can appear as dark spots that detract from the aesthetic provided by the resin-based sculpture.

Accordingly, there are a number of disadvantages in resin-based sculptures that can be addressed.

BRIEF SUMMARY OF THE INVENTION

One or more implementations of the present invention solve one or more of the foregoing or other problems in the art with resin-based sculptures that help magnify the aesthetic features of resin-based materials included therein. For example, one or more implementations of the present invention include resin-based sculptures that reduce or eliminate the visibility of hardware. In particular, one or more implementations include resin-based sculptures with colored resin-based fasteners that blend in with the resin of the sculptures. Such colored resin-based fasteners can adequately and securely couple resin pieces of the sculpture without adding an unpleasing aesthetic.

For example, a resin-based sculpture in accordance with one implementation of the present invention includes a plurality of resin strips, and a plurality of resin-based fasteners securing the plurality of resin strips together. One or more resin strips of the plurality of resin strips are shaped to form a decorative design. Additionally, a color of one or more resin-based fasteners of the plurality of resin-based fasteners match a color of the one or more resin strips that are secured by the plurality of resin-based fasteners.

Another example includes a resin-based lighting fixture comprising a plurality of resin pieces. Furthermore, such resin-based lighting fixture includes a plurality of resin-based rivets securing the plurality of resin pieces together. The one or more resin pieces of the plurality of resin pieces are shaped to form a decorative design. Also, a color of one or more resin-based rivets matches a color of the one more resin pieces secured by the one or more resin-based rivets and/or a color of an overlapping area formed by the one or more resin pieces overlapping each other. The resin-based lighting fixture also includes a lighting source at least partially surrounded by the plurality of resin pieces.

In addition to the foregoing, a method of forming resin-based sculptures in accordance with one implementation involves cutting a plurality of resin pieces from a resin sheet. The method also involves heating the resin pieces and shaping two or more of the resin pieces. Furthermore, the method involves securing a first resin piece of the two or more resin pieces to a second resin piece of the two or more resin pieces using a resin-based fastener having a color the same as a color of the first and second resin pieces. The method further involves assembling the resin pieces about a mounting fixture.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. For better understanding, the like elements have been designated by like reference numbers throughout the various accompanying figures. Understanding that these drawings depict only typical embodiments of the invention and are not therefore to be considered to be limiting of its scope, the invention will be described and explained with additional specificity and detail through the use of the accompanying drawings in which:

FIG. 1A illustrates a perspective view of a resin-based rivet in accordance with one implementation of the present invention;

FIG. 1B illustrates a bottom view of the resin-based rivet of FIG. 1A;

FIG. 1C illustrates a cross-sectional view of the resin-based rivet of FIG. 1A;

DETAILED DESCRIPTION OF THE PREFERRED EMBODIMENTS

Figure 1D:
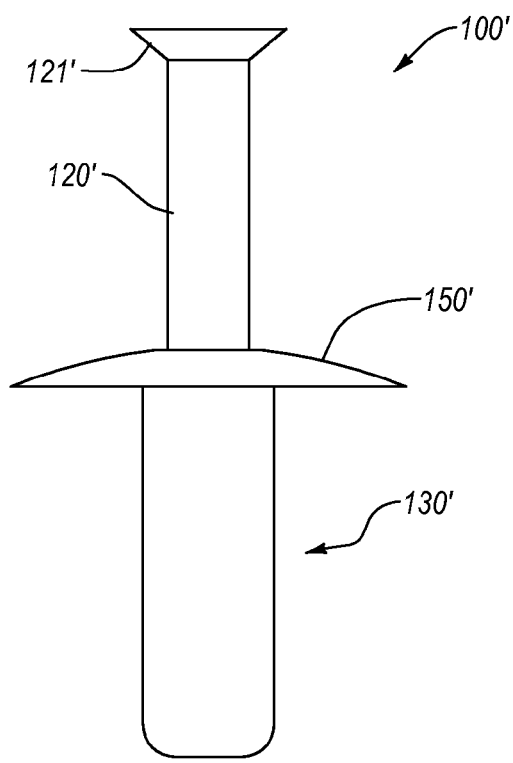
FIG. 1D illustrates a side view of a resin-based rivet in accordance with one or more implementations of the present invention.

The present invention is directed toward resin-based sculptures that help magnify the aesthetic features of resin-based materials included therein. For example, one or more implementations of the present invention include resin-based sculptures that reduce or eliminate the visibility of hardware. In particular, one or more implementations include resin-based sculptures with colored resin-based fasteners that blend in with the resin of the sculptures.

One will appreciate in light of the disclosure herein that one or more implementations of the present invention can provide aesthetically pleasing resin-based sculptures. For instance, one or more implementations include resin-based lighting fixtures that are hand shaped into aesthetically pleasing configurations. Furthermore, the resin-based lighting fixtures can help magnify the aesthetic features of the resin materials used in the lighting fixtures. Indeed, one or more implementations help magnify the form, texture, color, transparency, and combinations thereof of the resin materials. In addition, one or more implementations reduce or eliminate the visibility of hardware that may otherwise detract from the aesthetics of the lighting fixture and/or resin materials.

In particular, one or more implementations include resin-based fasteners that secure or otherwise couple resin pieces (e.g., strips, panels) together. For instance, the resin-based fasteners may be colored to match the color of the resin pieces secured thereby. By matching the color of the resin-based fasteners to the resin pieces, the resin-based fasteners can blend in with the resin pieces, thereby reducing the visibility of the fasteners. In still further implementations, the resin-based fasteners comprise a similar color, but a lighter shade, than the resin pieces they are securing. In such implementations, when the resin-based sculpture is illuminated, the lighter shade fasteners can blend in with the resin pieces. In yet further implementations, the resin-based fasteners are transparent or translucent and colored to further reduce their visibility. In addition to the foregoing, in one or more implementations the use of resin-based fasteners can reduce the overall weight of a sculpture.

In at least one implementation, the resin-based fasteners can be resin-based rivets, which can secure two or more resin pieces or panels together. For instance, FIG. 1A illustrates an exemplary resin-based rivet 100. As an initial matter, the terms "resin," or "resin-based," as used herein, refer to fasteners, panels, or strips, comprising a substrate of one or more layers or sheets formed from thermoplastic polymers (or alloys thereof). Specifically, such materials can include, but are not limited to, polyethylene terephthalate (PET), polyethylene terephthalate with glycol-modification (PETG), acrylonitrile butadiene-styrene (ABS), polyvinyl chloride (PVC), polyvinyl butyral (PVB), ethylene vinyl acetate (EVA), polycarbonate (PC), styrene, polymethyl methacrylate (PMMA), polyolefins (low and high density polyethylene, polypropylene), thermoplastic polyurethane (TPU), cellulose-based polymers (cellulose acetate, cellulose butyrate or cellulose propionate), nylon, acetal, or the like.

More specifically, the resin-based rivet 100 is a blind rivet (i.e., a rivet that can be fastened with access to only one side of the objects being secured together). Consequently, as further described below, a manufacturer can secure together two objects, such as resin pieces, from an outward-facing or viewing side of such objects. In alternative implementations, the rivet can comprise a solid rivet or another type of rivet. Furthermore, one will appreciate that, generally, the resin-based rivets are not limited to blind rivets.

In one example, the resin-based rivet 100 can include a main body 110 and a mandrel 120. The main body 110 can comprise a head 150 and a blind end 130. In at least one implementation, the mandrel 120 can move relative to the main body 110, thereby fastening the resin-based rivet 100 within an opening in two or more resin pieces. For instance, a manufacturer can advance the mandrel 120 in a distal direction relative to the main body 110 to secure the resin-based rivet 100 within openings in the resin pieces. The term "distal" direction, as used herein in connection with the resin-based rivet 100, shall refer to a direction toward the blind end 130 of the main body 110.

In one or more implementations, the main body 110 (e.g., the head 150 of the main body 110) can include an opening 140 that can facilitate advancement of the mandrel 120 relative to the main body 110. The opening 140 can have substantially the same cross-sectional size and/or shape as the mandrel 120. For example, the opening 140 can have an approximately circular cross-sectional shape. Likewise, the mandrel 120 can have a substantially cylindrical shape (i.e., a circular cross-section) and can be substantially the same size as the opening 140.

Hence, in at least one implementation, the mandrel 120 can freely slide within the opening 140 in the distal direction. Alternatively, the mandrel 120 can have a pressed or tight fit within the opening 140. Accordingly, the mandrel 120 can frictionally slide within the opening 140, in a manner that may require a predetermined amount of force to push or advance the mandrel 120 relative to the main body 110. Thus, once fully advanced, the mandrel 120 can remain secured or fixed within the opening 140. Specifically, in at least one implementation, advancement of the mandrel 120 within the opening 140 can elastically deform the mandrel 120 and/or a portion of the main body 110, such that the opening 140 compresses the mandrel 120 therein.

Moreover, the manufacturer can generally secure or fix the mandrel 120 relative to the main body 110 (e.g., once the mandrel 120 is in the fully advanced position). For instance, the manufacturer can glue or weld the mandrel 120 within the opening 140. In any event, the mandrel 120 can remain fixed or substantially stationary within the opening 140, once the mandrel 120 is in the fully advanced position.

Implementations also include the main body 110 that has the head 150 coupled to or integrated with the blind end 130. In one example, the blind end 130 can be split into two or more legs 160 (e.g., legs 160a, 160b). The legs 160 can secure the resin-based rivet 100 within the openings of the resin pieces, thereby also securing the two resin pieces together. As further described below, the legs 160 can move outward relative to an axis of the resin-based rivet 100. In additional or alternative implementations, the blind end 130 can have one, three, four, or more legs.

In any event, in one or more implementations, the blind end 130 can be hollow. Thus, the mandrel 120 can pass through the opening 140 and enter the blind end 130. As the mandrel 120 enters the blind end 130, the mandrel 120 can push one or more portions of the blind end 130 outward.

For example, as noted above, the legs 160 can move outward relative to the axis of the resin-based rivet 100. Hence, the mandrel 120 can push the legs 160 outward relative to each other, when the mandrel 120 enters the blind end 130. Likewise, the mandrel 120 can push any number of legs 160 outward relative to each other, as the mandrel 120 enters the blind end 130. Similarly, the mandrel 120 can push outward an outer wall of a single leg 160 that can comprise the blind end 130.

Additionally, as illustrated in FIGS. 1B-1C, the resin-based rivet 100 can have a conical opening 170 formed about interior portions of the legs 160. In other words, the legs 160 can have cored-out portions that together form a conical recess therebetween. As the mandrel 120 moves along the opening 170, the mandrel 120 can push the legs 160 away from each other, thereby securing the resin-based rivet 100 within the holes of the resin pieces (e.g., resin panels or strips). In any event, the legs 160 can include the opening 170 configured in a manner that allows the mandrel 120 to enter such opening 170 and to spread the legs 160 outward, away from each other.

In one or more implementations, the resin-based rivet 100 also can incorporate slots 180, cored out along respective lengths of the legs 160. As noted above, the resin-based rivet 100 can allow light to pass therethrough, which can allow the resin-based rivet 100 to blend in with the resin pieces secured thereby. Accordingly, the slots 180 can reduce thickness of the legs 160 as well as facilitate improved light transmission through the resin-based rivet 100.

To use the resin-based rivet 100, a user or manufacturer can insert the resin-based rivet 100 into holes in the resin pieces to be joined. Subsequently, the manufacturer can draw or force the mandrel 120 into the head 150 (e.g., the manufacturer can use a riveting gun). As noted above, this expands the blind end 130 of the resin-based rivet 100. Thereafter, the mandrel 120 can remain positioned within the head 150 and the blind end 130, such as to maintain the blind end 130 in an expanded configuration (e.g., the legs 160 being spread outward apart from each other).

In additional or alternative implementations, at least a portion of the mandrel 120 can snap off after expansion of the blind end 130. In any case, the blind end 130 can remain in the expanded configuration. Moreover, once the blind end 130 is in the expanded configuration, the mandrel 120 can be substantially flush with a top of the head 150.

Furthermore, it should be appreciated that a particular size and shape of the head 150 may vary from one implementation to another. For example, the head 150 can have a first ratio of area to thickness thereof, as illustrated in FIG. 1C. Alternatively, as illustrated in FIG. 1D, a resin-based rivet 100' can incorporate a head 150' that has a second ratio of area to thickness thereof. Except as otherwise described herein, the resin-based rivet 100' and its components and elements can be the similar to or the same as the resin-based rivet 100 (FIG. 1A-1C) and its respective components and elements. For instance, the resin-based rivet 100' can include a blind end 130' that may be the same as the blind end 130 of the resin-based rivet 100 (FIGS. 1A-1C).

In one implementation, however, the second ratio can be larger than the first ratio. In other words, the head 150' can be thinner and/or can have a larger area than the head 150 (FIGS. 1A-1C). For example, the head 150' may have a thickness in one or more ranges of approximately 0.015"-0.030", 0.020"-0.070", and 0.050"-0.150". In addition, the head 150' may have a diameter of approximately 0.100"-0.200", 0.187"-0.312", and 0.250-0.375. In other implementations, the head 150' may have a greater thickness than 0.150" or a smaller thickness than 0.015". Furthermore, the head 150' may have a larger diameter than 0.375" or a smaller diameter than 0.100".

In one or more implementations, the resin-based rivet 100' can incorporate a mandrel 120' that may have a countersinking top portion 121'. More specifically, the top portion 121' can enter a corresponding opening (e.g., a countersink) in the head 150'. Moreover, the top portion 121' may have a tapered bottom, which may allow the top portion 121' to align with the corresponding countersink in the head 150'.

Thus, the top of the mandrel 120' may form a more uniform and/or apparently uninterrupted surface with the top of the head 150', which can facilitate concealing the resin-based rivet 100' relative to the surface(s) of resin pieces connected thereby. As described herein, in at least one implementation, the resin-based rivet 100' may be substantially clear or transparent. Accordingly, eliminating or limiting defects, imperfections, and interruptions on the visible surface of the resin-based rivet 100' (e.g., by reducing or eliminating a gap between the mandrel 120' and the top surface of the head 150') also can reduce or eliminate reflective surfaces, which may make the resin-based rivet 100' more apparent. Accordingly, the above-described configuration of the mandrel 120', among other things, can aid in efficiently concealing the resin-based rivet 100' against the surface of the resin piece(s) connected thereby.

Figure 2:
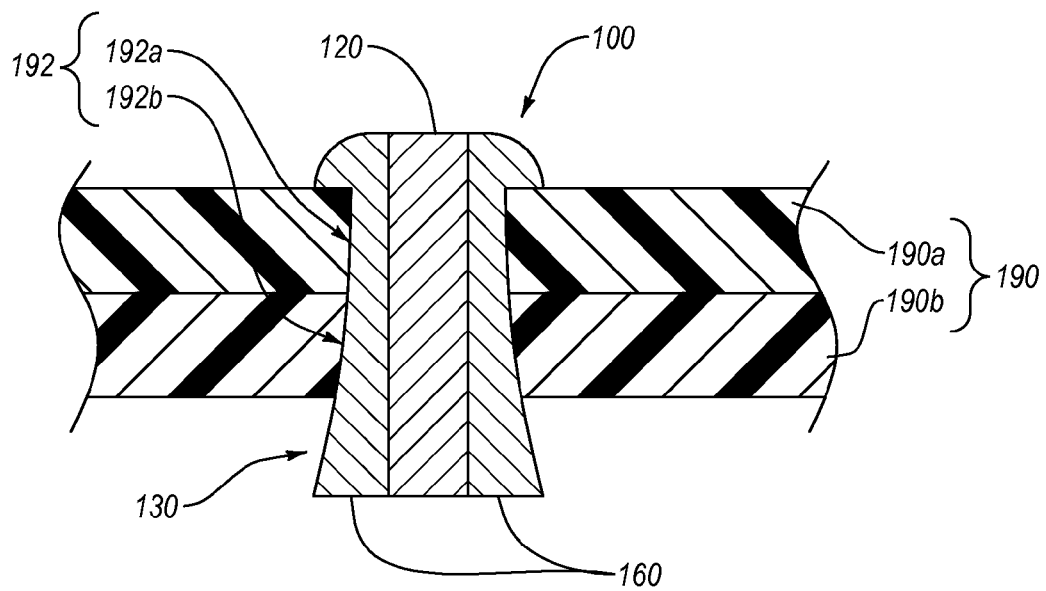
FIG. 2 illustrates a cross-sectional view of an installation of a resin-based rivet of FIG. 1A in accordance with one implementation of the present invention.

An exemplary installation of the resin-based rivet 100 is illustrated in FIG. 2. Specifically, FIG. 2 illustrates the resin-based rivet 100 in the expanded configuration, securing two adjacent resin pieces 190 (i.e., resin pieces 190a, 190b). It should be appreciated that the resin-based rivet 100' (FIG. 1D) may be installed in a similar or the same manner as the resin-based rivet 100.

As described above, the mandrel 120 of the resin-based rivet 100 can move in the distal direction, toward and/or into the blind end 130, thereby pushing the legs 160 outward and securing the resin-based rivet 100 within top and bottom openings 192a, 192b of the resin pieces 190. For instance, in the expanded configuration, at least a portion of the blind end 130 can be larger than the bottom opening 192b, such as to prevent withdrawal of the resin-based rivet 100 from the openings 192. Accordingly, the resin-based rivet 100 can remain secured within the openings 192 and can limit or prevent relative movement of the resin pieces 190a and 190b.

Additionally or alternatively, the legs 160 can press outward and against walls of the openings 192. For example, the legs 160 can elastically deform and engage the walls of the openings 192, thereby maintaining the resin-based rivet 100 substantially stationary or fixed relative to the resin pieces 190. In one or more implementations, the mandrel 120, legs 160, a portion of the openings 192, and combinations thereof can plastically deform, and such deformation can secure the resin-based rivet 100 within the openings 192.

Moreover, in at least one implementation, the mandrel 120 can remain in the blind end 130. Thus, the mandrel 120 can aid in maintaining the blind end 130 in the expanded configuration. In any event, the resin-based rivet 100 can remain secured within the openings 192 in a manner that prevents or limits relative movement of the resin pieces 190a, 190b.

Figure 3A:
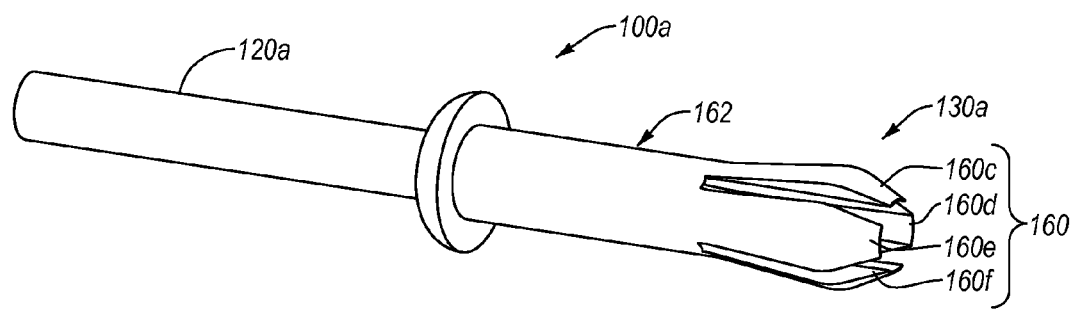
FIG. 3A illustrates a perspective view of a resin-based rivet in accordance with another implementation of the present invention.

As noted above, implementation of the present invention can include resin-based rivets with more than two legs. Likewise, configurations of the blind end of the resin-based rivet, generally, can vary from one implementation to another. Moreover, one will appreciate in light of the disclosure herein that the resin-based rivets can comprise any number of different sizes, shapes, colors, shades, and configurations. For example, FIG. 3A illustrates another implementation of a resin-based rivet 100a, which includes an elongated blind end 130a.

Except as otherwise described herein, the resin-based rivet 100a and its components and elements can be similar to or the same as the resin-based rivet 100 (FIGS. 1A-1C) and its respective components and elements. In one implementation, the blind end 130a can incorporate a tubular portion 162, which can transition into multiple legs 160 (i.e., legs 160c, 160d, 160e, 160f). In one or more instances, the tubular portion 162 can provide an improved or more precise location for the resin-based rivet 100a within the opening in the resin pieces connected thereby.

Figure 3B:
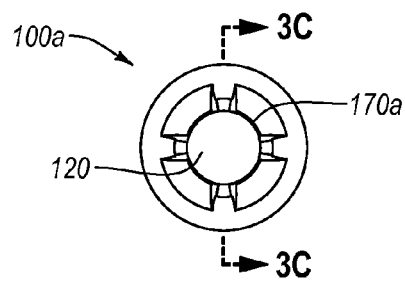
FIG. 3B illustrates a bottom view of the resin-based rivet of FIG. 3A.
Figure 3C:
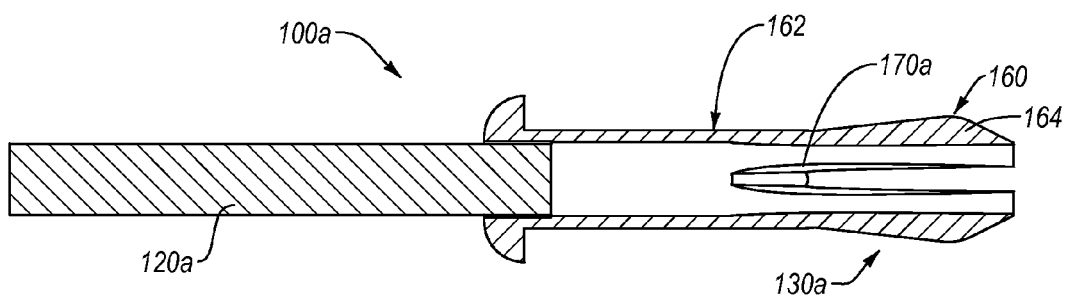
FIG. 3C illustrates a cross-sectional view of the resin-based rivet of FIG. 3A.

In one or more implementations, the mandrel 120 can enter the tubular portion 162 of the blind end 130a and can proceed further in the distal direction. Similar to the resin-based rivet 100 (FIGS. 1A-1C) the resin-based rivet 100a can include a tapered or conical opening 170a, shown in FIGS. 3B, 3C. As the mandrel 120a enters the opening 170a, the mandrel 120a can push legs 160 outward, away from each other. As such, the mandrel 120a can expand the blind end 130a into an expanded configuration, in which the resin-based rivet 100a can secure multiple resin pieces together.

Additionally or alternatively, the opening 170a can be substantially cylindrical and can have a size sufficient to accommodate the mandrel 120a therein. For instance, the manufacturer can advance the mandrel 120a into the opening 170a, thereby pushing the legs 160 outward and securing the blind end 130a in the expanded configuration. In one example, the legs 160 can have outward protruding portions 164, which can secure the resin-based rivet 100a within the openings of the resin pieces.

Moreover, the legs 160 can flexibly couple to or be integrated with the tubular portion 162 of the blind end 130a. Consequently, the legs 160 can flex inward or collapse together in a manner that allows insertion of the blind end 130a into the openings of the resin pieces. Subsequently, after inserting the blind end 130a into the holes of the resin pieces, the manufacturer can advance the mandrel 120a into the opening 170a to expand the legs 160, thereby securing the resin-based rivet 100a within the holes as well as securing the resin pieces together.

Figure 3D:
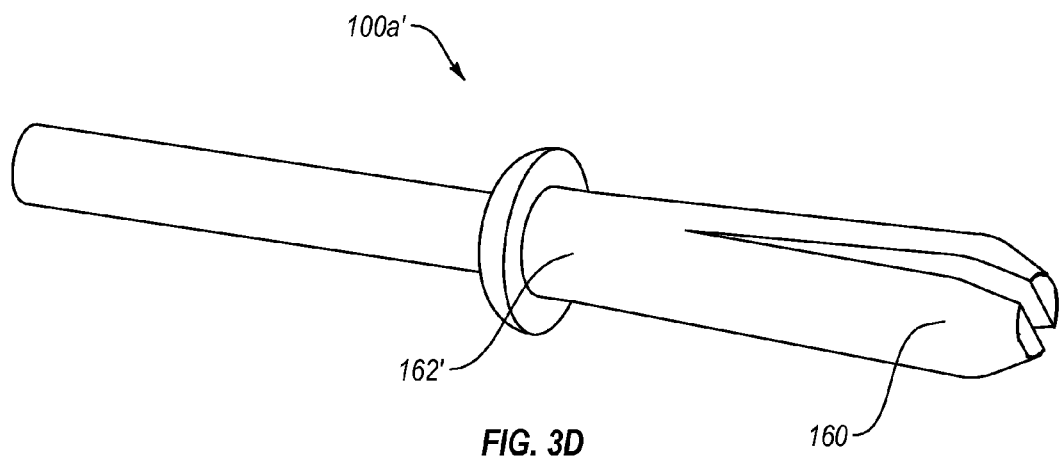
FIG. 3D illustrates a perspective view of a resin-based rivet in accordance with one other implementation of the present invention.

As noted above, the resin-based rivet 100a may have any number of legs 160, which may vary from one implementation to the next. One implementation includes a resin-based rivet 100a' that has two legs 160, as shown in FIG. 3D. Except as described herein, the resin-based rivet 100a' and its components and elements can be similar to or the same as any one of the resin-based rivet 100, 100', 100a (FIGS. 1A-3C) and their respective components or elements. For instance, similar to the resin-based rivet 100a (FIGS. 3A-3C), the resin-based rivet 100a' may include a tubular portion 162. In any event, the resin-based rivet 100a' may couple two resin pieces in a similar or the same manner as the resin-based rivet 100a (FIGS. 3A-3C) and may be substantially invisible or unnoticeable against the surface(s) of such resin pieces.

Figure 4:
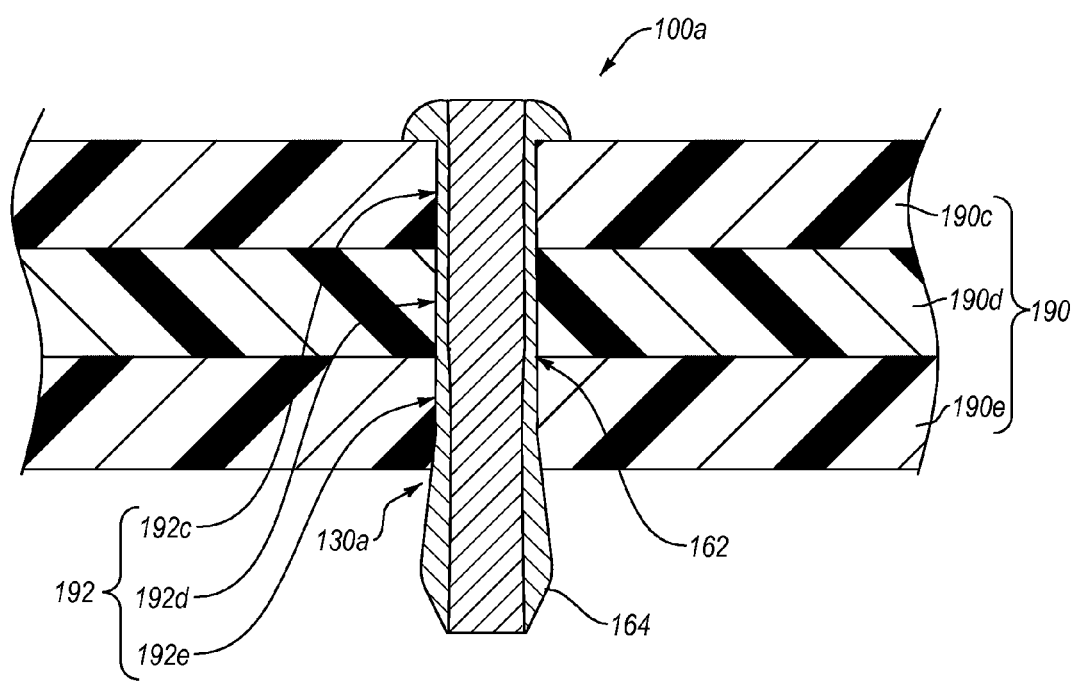
FIG. 4 illustrates a cross-sectional view of an installation of a resin-based rivet of FIG. 3A in accordance with one implementation of the present invention.

For example, as illustrated in FIG. 4, the resin-based rivet 100a can couple together multiple resin pieces 190. It should be also appreciated that the resin-based rivet 100a' (FIG. 3D) can couple the resin pieces 190 in a similar manner. In particular, the resin-based rivet 100a can couple three resin pieces 190c, 190d, 190e. Furthermore, as noted above, the tubular portion 162 of the blind end 130a can provide a precise location of the resin-based rivet 100a within openings 192 (i.e., openings 192c, 192d, 192e). Accordingly, the resin-based rivet 100a can have less play or movement within the openings 192 of the resin pieces 190, which can facilitate more precise alignment of the resin pieces 190c, 190d, and/or 190e relative to each other upon insertion of the resin-based rivet 100a into the openings 192. Additionally, once the mandrel 120a is inserted into the opening 170 and the legs 160 are expanded, the protruding portions 164 of the blind end 130a can be larger than the bottom opening 192e, such as to prevent withdrawal of the resin-based rivet 100a from the openings 192. Accordingly, the resin-based rivet 100a can remain secured within the openings 192 and can limit or prevent relative movement of the resin pieces 190c, 190d, 190e.

FIGS. 1A-1C and 3A-3C illustrate exemplary resin-based rivets 100, 100a. One will appreciate that the resin-based fasteners of the present invention are not limited to rivets. The resin-based fasteners of one or more implementations of the present invention can comprise any number of different types of fasteners. Resin-based fasteners of one or more implementations can include, but are not limited to, screws, clips, brackets, zip ties, bolts, etc.

Figure 5:
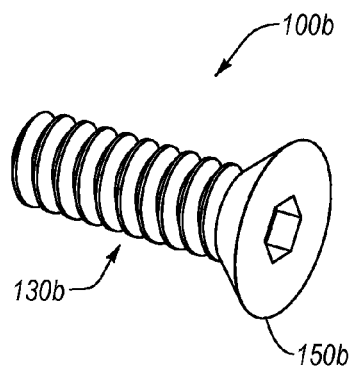
FIG. 5 illustrates a perspective view of a resin-based fastener in accordance with one implementation of the present invention.

For example, FIG. 5 illustrates a resin-based screw 100b, which incorporates a head 150b and a threaded portion 130b. The resin-based screw 100b can fasten together two or more resin pieces in any number of ways. In one implementation, one or more of the resin pieces can incorporate a threaded opening, which can accept and secure the threaded portion 130b of the resin-based screw 100b. Additionally or alternatively, the manufacturer can place a resin-based nut on an inward facing portion of the resin pieces and can thread the resin-based screw 100b into the resin-based nut, to secure the resin pieces together. In any event the resin-based screw 100b can removably or permanently couple two or more resin pieces together.

Moreover, the resin-based nut also can comprise resin material. Particularly, the resin-based nut and the resin-based screw 100b can comprise similar resin material, which can have similar or the same transparency, translucency, color, hue, and any number of other visual qualities. Thus, as further described below, the resin-based screw 100b and/or the resin-based nut can blend in with the resin pieces secured thereby.

In at least one implementation, at least a portion of the resin-based screw 100b and/or of the resin-based nut comprises non-resin material. For example, the resin-based screw 100b can comprise a metallic (e.g., steel, aluminum, etc.) screw at least partially encapsulated in a resin material. More specifically, resin material can encapsulate portions of the metallic screw visible to a viewer of the resin-based sculpture. Moreover, the color, shade, and texture of the resin material can match the color, shade, and/or texture of the resin pieces that form the resin-based sculpture.

Alternatively, the resin-based screw 100b can comprise a resin portion with one or more metallic inserts secured therein or overmolded thereby. For example, such metallic inserts can improve the strength of the resin-based screw 100b. In one or more implementations, the resin-based screw 100b can have inserted metallic threads, which can provide improved strength and holding power of the resin-based screw 100b (as compared with resin threads).

Figure 6:
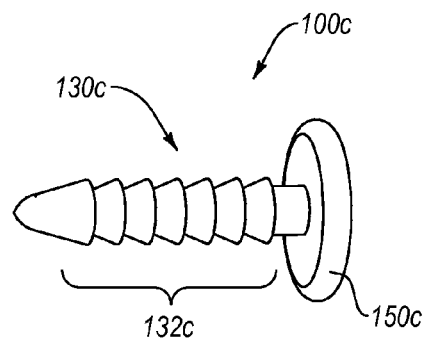
FIG. 6 illustrates a perspective view of a resin-based fastener in accordance with another implementation of the present invention.

Another example of a resin fastener is illustrated in FIG. 6. In particular, FIG. 6 illustrates a resin-based clip 100c. For instance, the manufacturer can push the resin-based clip 100c through a hole or an opening in the resin pieces or strips, to secure together such resin pieces. The resin-based clip 100c can include a head 150c and a protrusion or a spine 130c extending outward from the head 150c. In addition, the resin-based clip 100c can include multiple flanges 132c on the spine 130c.

The flanges 132c of the resin-based clip 100c can then prevent the resin resin-based clip 100c from pulling out of the hole. In other words, the flanges 132c can engage one or more holes or openings in the resin pieces, thereby securing the resin-based clip 100c within such openings. Consequently, as the manufacturer secures the resin-based clip 100c within the openings of the resin pieces, the resin-based clip 100c can secure together two or more resin pieces. It should be appreciated that, similar to the resin-based rivets 100, 100a and the resin-based screw 100b (FIGS. 1A-1C, 3A-3C, and 5), the resin-based clip 100c can comprise resin material that can match or blend in with the resin pieces coupled thereby.

Figure 7A:
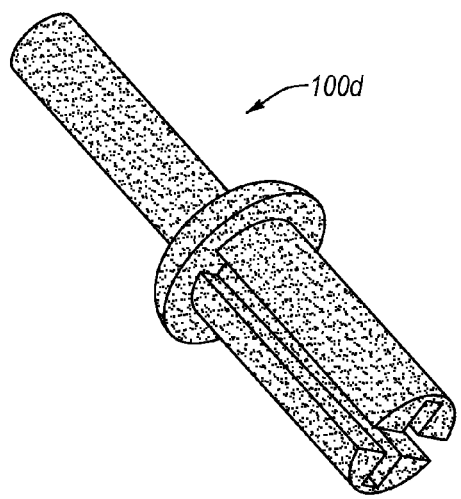
FIG. 7A illustrates a perspective view of a resin-based rivet in accordance with yet another implementation of the present invention.
Figure 7B:
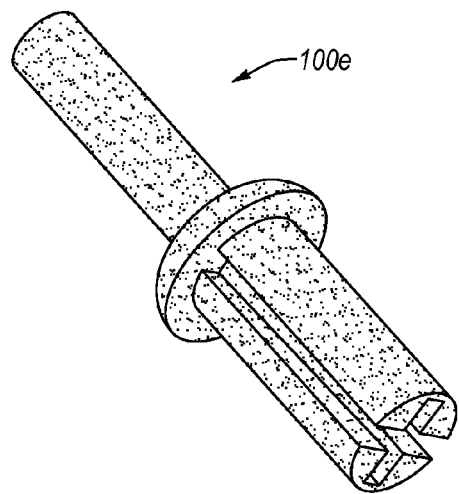
FIG. 7B illustrates a perspective view of a resin-based rivet in accordance with still one other implementation of the present invention.

For example, FIGS. 7A and 7B illustrate colored resin-based fasteners that can blend in with the resin pieces secured thereby. Particularly, FIGS. 7A and 7B illustrate colored resin-based rivets 100d, 100e, respectively. The resin-based rivets 100d, 100e can include the same features and function as any one of the resin-based fasteners described above, including resin-based rivet 100, 100a, resin-based screw 100b, and resin-based clip 100c (FIGS. 1A-1C, 3A-3C, 5, and 6).

The resin-based rivets 100d, 100e, however, can have the same or similar color and/or shade thereof as the resin pieces coupled by such resin-based rivets 100d, 100e. In one example, the resin-based rivet 100e has a lighter shade of the same color as the resin-based rivet 100d, which can have a darker shade of that color. In other words, resin-based rivet 100d is the same color as the resin-based rivet 100e, but is a darker shade of that color. Accordingly, the manufacturer can select appropriate color and/or shade of the resin-based rivet as appropriate for a particular application.

Furthermore, the manufacturer can color white resin-based rivets, for instance, by applying a dye to the white resin-based rivets. As such, the manufacturer can control the shade of the resin-based rivets 100d, 100e by controlling the amount of time the resin-based rivet 100d and the resin-based rivet 100e are mixed with or otherwise exposed to the dye. In alternative implementations, the resin-based rivets 100d, 100e and/or portions thereof can be extruded or molded in a particular color and/or shade, which the manufacturer can premix with thermoplastic resin pellets prior to extrusion or molding. As explained below, the ability to color and control the shade of the resin-based fasteners (e.g., resin-based rivets) can allow the resin-based fasteners to blend in with the resin pieces of the resin-based sculpture.

Figure 8A:
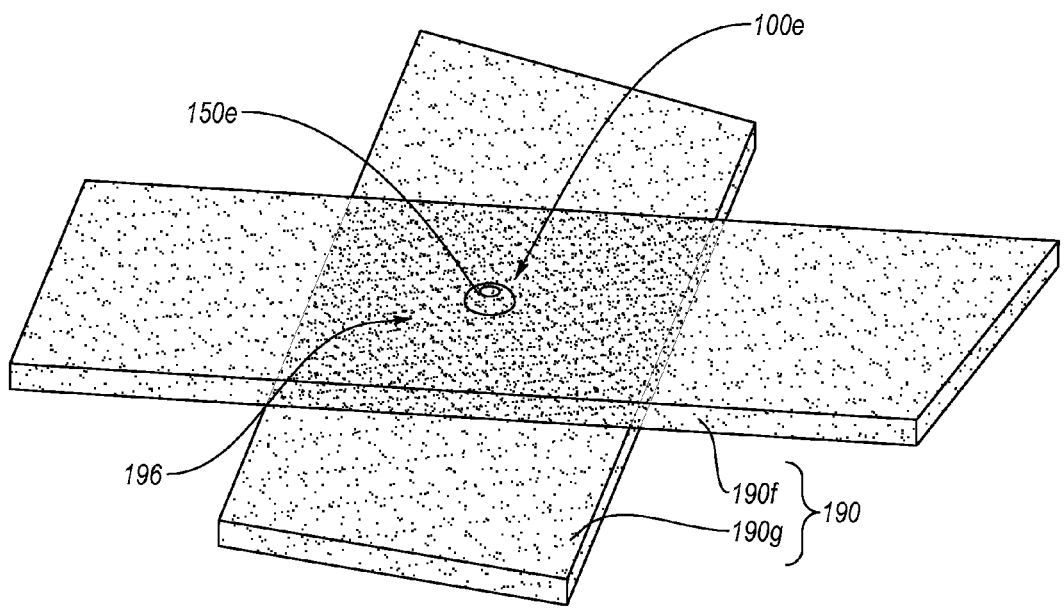
FIG. 8A illustrates a top perspective view of two resin pieces secured by a resin-based rivet in accordance with one implementation of the present invention.
Figure 8B:
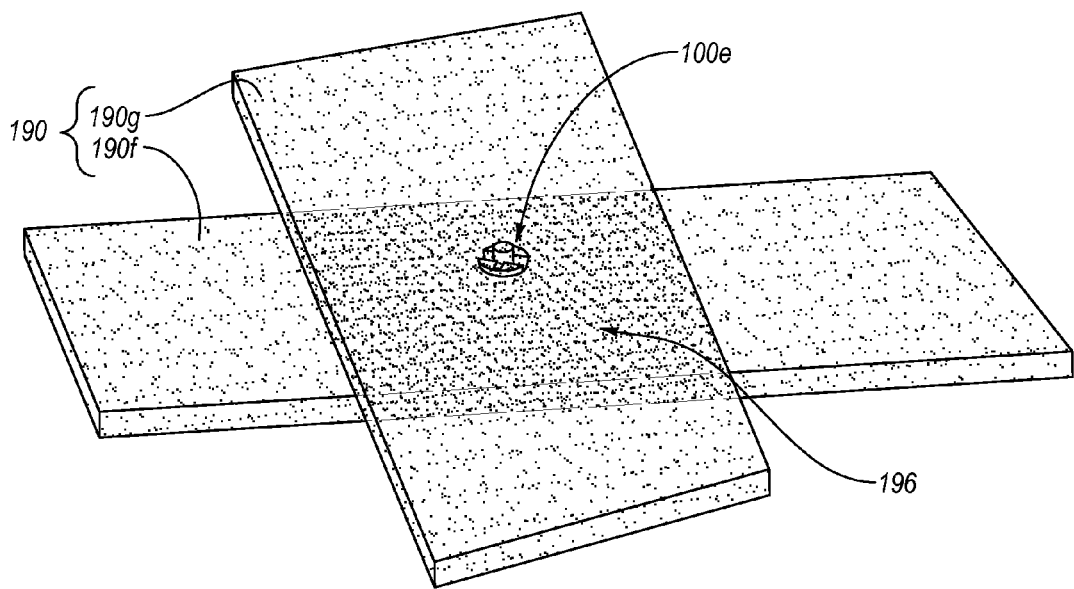
FIG. 8B illustrates a bottom perspective view of the two resin pieces secured by the resin-based rivet of FIG. 8A.

FIGS. 8A-8B illustrate an exemplary connection of two resin pieces 190f, 190g. Particularly, the resin-based rivet 100e can pass through and connect together the resin piece 190f and the resin piece 190g. For example, to secure the resin pieces 190f, 190g together, the manufacturer can drill a hole through each of the resin pieces 190f, 190g. Such hole or opening in the resin pieces 190f, 190g can facilitate insertion of a resin fastener therethrough, which can allow the manufacturer to secure together the resin pieces 190f, 190g.

In at least one implementation, the manufacturer can then insert the resin-based rivet 100e through the opening in the resin pieces 190f, 190g and can secure the resin-based rivet 100e therein. As noted above, to secure the resin-based rivet 100e within the openings of the resin pieces 190f, 190g, the manufacturer can force the mandrel of the resin-based rivet 100e in the distal direction, thereby reconfiguring the resin-based rivet 100e into the expanded configuration. Accordingly, the manufacturer can secure the resin-based rivet 100e within the openings in the resin pieces 190f, 190g, which also can secure the resin pieces 190f, 190g together.

In addition, the resin-based rivet 100e can have the same color as the resin pieces 190f, 190g. As such the resin-based rivet 100e can blend in with the resin pieces 190f, 190g. In other words, the resin-based rivet 100e can fasten the resin pieces 190f, 190g together, in a manner that may not detract a viewer from the aesthetics of the resin pieces 190f, 190g. As described below in more detail, the resin-based rivet 100e can be substantially unnoticeable to the viewer on the resin piece 190f and/or resin piece 190g.

In one or more implementations, the resin-based rivet 100e can have the same color as the resin pieces 190f, 190g. In other implementations, however, the resin-based rivet 100e can have a shade that differs from the shade of the resin pieces 190f, 190g. For example, the resin pieces 190f, 190g can be translucent or transparent. As such, when the manufacturer places the resin pieces 190f, 190g on top of each other, an overlapping area 196 formed at the intersection of the resin pieces 190f, 190g may appear darker than each individual resin piece 190f and/or 190g. Accordingly, the manufacturer can select the resin-based rivet 100e that has a matching shade, which can blend in within the overlapping area 196.

Additionally, transparent or translucent resin pieces 190f, 190g can have different colors. Hence, the overlapping area 196 can have a color and/or shade that is different from any one of the colors of the resin pieces 190f, 190g. In such implementations, the resin-based rivet 100e can have a shade and/or color to match the color and shade of the overlapping area 196 of the resin pieces 190f, 190g. In other words, the resin-based rivet 100e can have a shade and color different from either or both of the individual resin pieces 190f, 190g, but which can closely match the shade and/or color of the overlapping area 196 of the resin pieces 190f, 190g.

Although the above described implementations include two overlapping resin pieces 190f, 190g, it be should appreciated that this disclosure is not so limited. Specifically, as noted above, the resin-based fasteners can couple together any number of resin pieces, which can vary from one implementation to another. Consequently, the resin-based fastener can match the particular shade and/or color of the overlapping area 196, which may be different from the particular resin pieces that form the overlapping area 196.

In still further implementations, the resin pieces 190f, 190g may form part of a resin-based lighting fixture, as explained in greater detail below. In such implementations, the resin pieces 190f, 190g as well as the overlapping area 196 may have a different shade and/or color when illuminated (i.e., when the lighting fixture is lit). For example, the resin piece 190f and/or resin piece 190g can comprise transparent and/or translucent resin, the shade of which, after illumination by lighting elements of the lighting fixture, can change. Hence, the manufacturer can use resin-based rivet 100e that can match the resin pieces 190f, 190g and/or the overlapping area 196 (formed by the resin pieces 190f, 190g) in an illuminated state (e.g., such that the resin-based rivet 100e blends in with the overlapping area 196).

Moreover, the lighting fixture can incorporate lighting elements that can emit light of any number of wave lengths. Accordingly, upon illumination, transparent and/or translucent resin pieces 190f, 190f as well as the overlapping area 196 formed thereby can appear a different color in the illuminated state than in un-illuminated state. Thus, the manufacturer also can match the color of the resin-based rivet 100e with the color of the resin pieces 190f, 190g and/or of the overlapping area 196 in the illuminated state (e.g., such that the resin-based rivet 100e blends in with the overlapping area 196 when the resin-based lighting fixture is illuminated).

In still further implementations, the resin-based rivet 100e can comprise a transparent material. The transparent material can allow the resin-based rivet 100e to have lighter shades. Furthermore, the transparent material can further allow the resin-based rivet 100e to blend in with the resin pieces 190f, 190g when used in resin-based sculptures. Thus, implementations can include resin-based a rivet 100e that comprises a substantially clear and transparent material. In additional or alternative implementations, the resin-based rivet 100e can comprise a substantially transparent material, which can have a hue or a color that can match the resin pieces 190f, 190g and/or the overlapping area 196.

Moreover, implementations of the present invention can include resin pieces 190f, 190g that at least partially comprise a substantially clear and transparent material. For example, the resin piece 190f and/or the resin piece 190g can comprise a clear and/or transparent or translucent thermoplastic resin that encapsulates one or more decorative objects or inter-layers of such objects (e.g., thatch, straw, fabric, etc.). Accordingly, a substantially clear and transparent resin-based rivet 100e can blend in with the resin pieces 190f, 190g, and the overlapping area 196 in a manner that the inter-layer of the resin pieces 190f, 190g is unobstructed by the resin-based rivet 100e.

In alternative implementations, the resin-based rivet 100e can be translucent or opaque. Furthermore, as indicated above, the resin-based rivet 100e, whether transparent, translucent, or opaque, can incorporate a color and a shade that can match the resin pieces 190f, 190g and/or the overlapping area 196. In any event, one will appreciate in light of the disclosure herein that the shade of the resin-based rivet 100e can be based at least in part on the transparency of the resin material of either the resin pieces 190f, 190g or the overlapping area 196.

Although the various levels of transparency, color, and/or shade described above referenced the resin-based rivet 100e, it should be appreciated that this disclosure is not so limited. More specifically, any one of the resin-based fasteners, such as the resin-based rivets 100, 100a, resin-based screw 100b, and resin-based clip 100c (FIGS. 1A-1C, 3A-3C, 5, and 6), can comprise a resin-based material that has the above noted properties. Accordingly, any one of the resin-based rivets 100, 100a, resin-based screw 100b, and resin-based clip 100c (FIGS. 1A-1C, 3A-3C, 5, and 6) can match and/or blend in with the resin pieces 190f, 190g and/or with the overlapping area 196, as may be desired by the manufacturer.

In one or more implementations, the resin-based fasteners (e.g., the resin-based rivet 100e) can have a thickness greater than the combined thicknesses of the resin pieces 190f, 190g. In particular, a head 150e of the resin-based rivet 100e can rest upon the outer surface of the first or outward facing resin piece 190f. A portion of the blind end of the resin-based rivet 100e can extend past the outer surface of the second resin piece 190g. Such thickness can allow the resin-based rivet 100e to secure the resin pieces 190f, 190g together.

At the same time, the increased thickness of the resin-based rivet 100e can increase the opacity of the resin-based rivet 100e, as compared with the combined thickness of the resin pieces 190a, 190b at the overlapping area 196. Such increased thickness also can distinguish resin-based rivet 100e or make the resin-based rivet 100e more visible against the background of the resin pieces 190f, 190g. One will appreciate in light of the disclosure herein that using a resin-based fastener or a resin-based rivet with a lighter shade and/or increased transparency, as compared with the resin pieces 190f, 190g, can help the resin-based fastener or the resin-based rivet to blend in with the resin pieces 190f, 190g and/or overlapping area 196.

In any event, any one of the resin-based fasteners described herein can secure together two or more resin pieces, such as strips, panels, sheets, and the like. Furthermore, when secured together, the resin strips, panels, and other resin pieces can form a resin-based sculpture. In particular, such resin-based sculptures can incorporate hidden or substantially obscured resin-based fasteners, which may not be visible and/or apparent to viewers of the resin-based sculptures.

FIGS. 9-13 illustrate exemplary resin-based sculptures. More specifically, FIGS. 9-13 illustrate resin-based lighting fixtures 200a-200d, respectively, formed from various resin pieces 190 secured together by resin-based fasteners. The resin pieces 190 can comprise any one, combinations, or alloys of the above-listed thermoplastic resin materials. As described below in further detail, the resin pieces 190 collectively can provide a shape, curvature, as well as overall design and aesthetic to the resin-based sculpture.

Figure 9A:
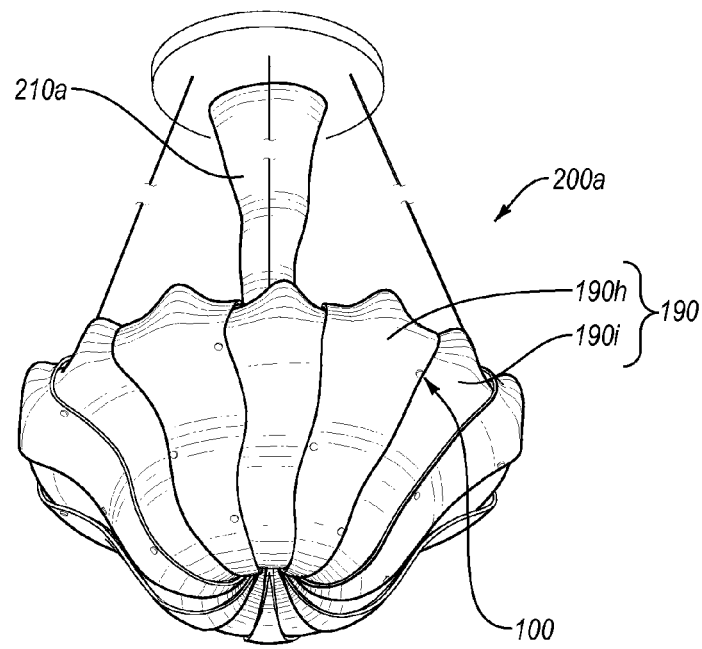
FIG. 9A illustrates a perspective view of a resin-based lighting fixture in accordance with one implementation of the present invention.
Figure 9B:
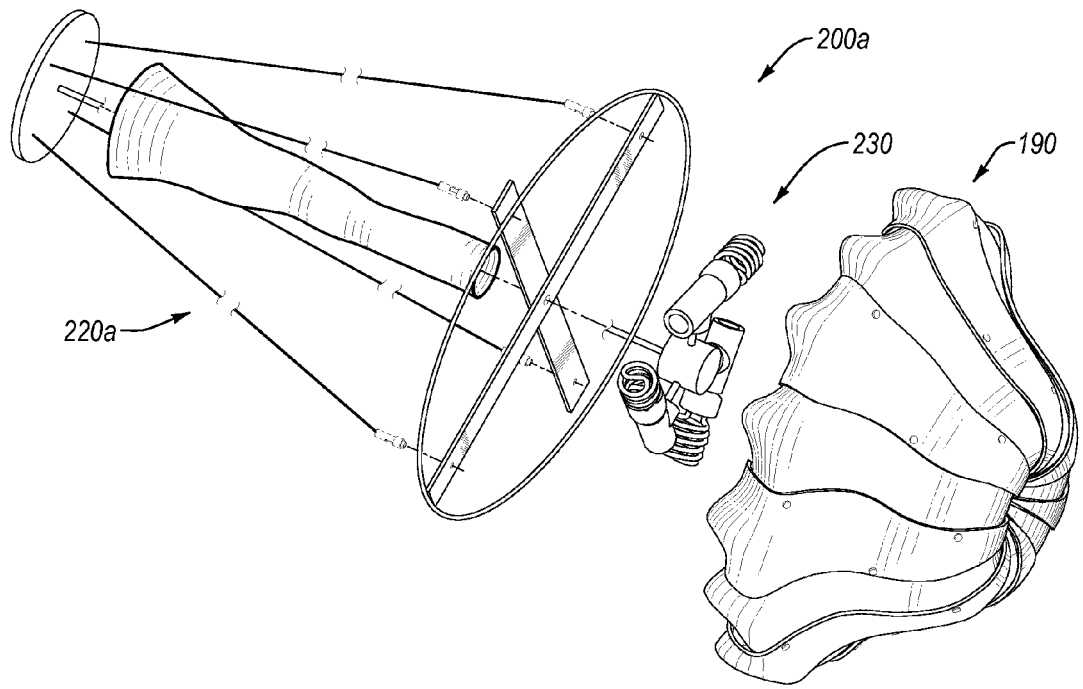
FIG. 9B illustrates an exploded perspective view of the resin-based lighting fixture of FIG. 9A.

For example, FIGS. 9A and 9B illustrate resin pieces 190 secured together by the resin-based rivet 100 in a manner that forms a mushroom-shaped resin-based lighting fixture 200a. For ease of description of the resin-based lighting fixture 200a, reference is made to the resin-based rivet 100. It should be appreciated, however, that additional or alternative implementations also can include any one of the above-described resin-based fasteners, which can secure the resin pieces 190 together.

As shown by FIG. 9A, in one or more implementations, any one of the resin pieces 190 can have a different curvature, shape, and/or size than, for instance, an adjacent resin piece 190. Thus, in one example, adjacent resin pieces 190h and 190i can have different shapes, sizes, curvatures, etc. Alternatively, some or all of the resin pieces 190 can have the same curvature, shape, and/or size as any or all of the other resin pieces 190.

The mushroom resin-based lighting fixture 200a can comprise a stand 210a, which can couple to the resin pieces 190. The stand 210a can provide sufficient support to secure the resin-based lighting fixture 200a on or to a support surface. For instance, the resin-based lighting fixture 200a can hang from a ceiling or other support surface. Alternatively, the resin-based lighting fixture 200a can stand upright on a support surface.

In at least one implementation, to allow a user to secure the resin-based lighting fixture 200a to a support surface, the resin-based lighting fixture 200a can include a mounting fixture 220a, illustrated in FIG. 9B. In other words, the resin-based lighting fixture 200a can include a plurality of resin pieces 190 secured to the mounting fixture 220a. Furthermore, the resin-based lighting fixture 200a can include a light source 230, which can illuminate the resin-base lighting fixture 200a.

In particular, the resin pieces 190 can extend about the light source 230. The light source 230 can comprise one or more light bulbs. For example, the light source 230 can comprise fluorescent light bulbs, incandescent light bulbs, light-emitting-diodes ("LEDs"), or any other suitable light bulbs or lighting elements. In any case, the light source 230 can illuminate the resin-based lighting fixture 200a as well as the resin pieces 190 and can provide a desirable aesthetic affect in addition to providing a source of light, which can illuminate a desired area or location.

As mentioned above, one or more resin-based rivets 100 can secure together overlapping resin pieces 190. Moreover, the resin-based rivets 100 can secure the resin pieces 190 to the mounting fixture 220a. Also, the resin-based rivets 100 can blend in against the background of the resin pieces 190. Consequently, in one or more implementations, when fully assembled, the resin-based lighting fixture 200a conceals most if not all mounting hardware from view.

The resin-based lighting fixture 200a can include any number of resin pieces 190. One will appreciate that a manufacturer can select the number of resin pieces 190 based on a desired shape or configuration for the resin-based lighting fixture 200a. In addition to the number of the resin pieces 190, the shape and form of the resin pieces 190 can vary, as mentioned above. For example, a manufacturer can form each or any one of the resin pieces 190 with varying curvature. Furthermore, the resin pieces 190 also can have varying widths, lengths, and overall dimensions.

In one or more implementations, the manufacturer can fold or form the resin pieces 190 in a manner to at least partially, or fully, conceal the light source 230. The resin pieces 190, however, can be flexible, and thus, allow a user to reposition or detach the resin pieces 190 to access the light source 230. Thus, the resin pieces 190 can provide an aesthetic function of concealing the light source 230 and/or the mounting fixture 220a of the resin-based lighting fixture 200a, without compromising the functional need of accessing the light source 230.

The resin-based sculptures or lighting fixtures may have any number of configurations and shapes, such as a blossom or flower, or a more abstract configuration. The configuration and style of the resin-based lighting fixture can be based at least partially on the shape, size, position, orientation, and number of the resin pieces 190. Thus, a manufacturer can select appropriate resin pieces 190 and can position, orient, and secure together such resin pieces 190 in order to produce a particularly shaped resin-based lighting fixture.

Figure 10A:
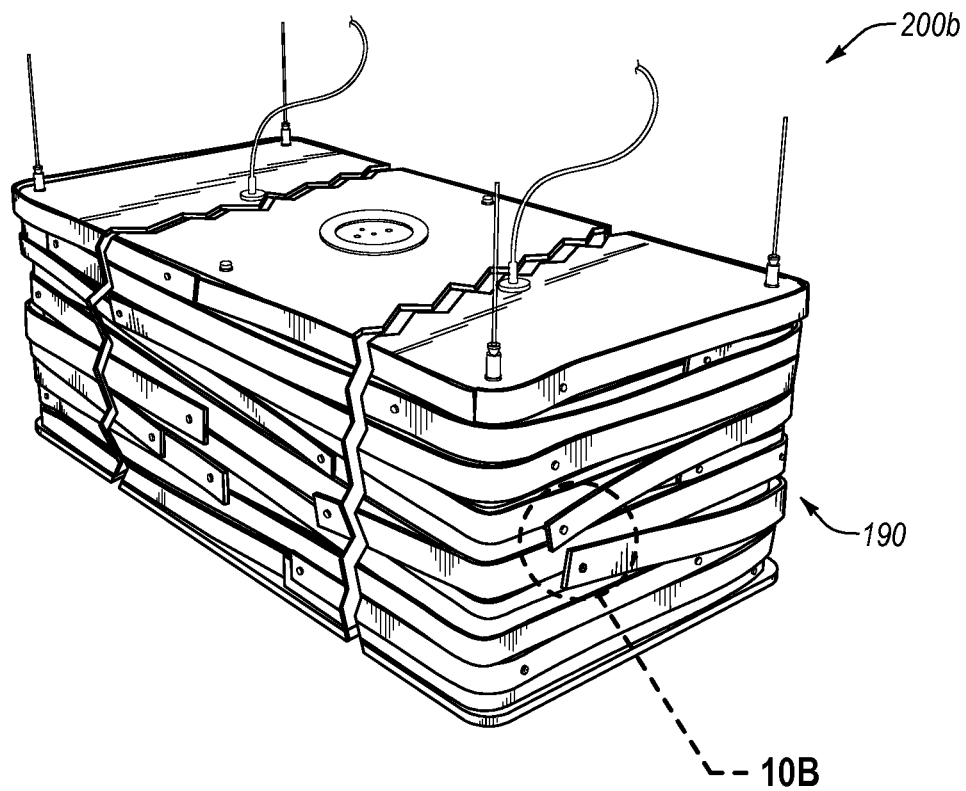
FIG. 10A illustrates a perspective view of a resin-based lighting fixture in accordance with another implementation of the present invention.
Figure 10B:
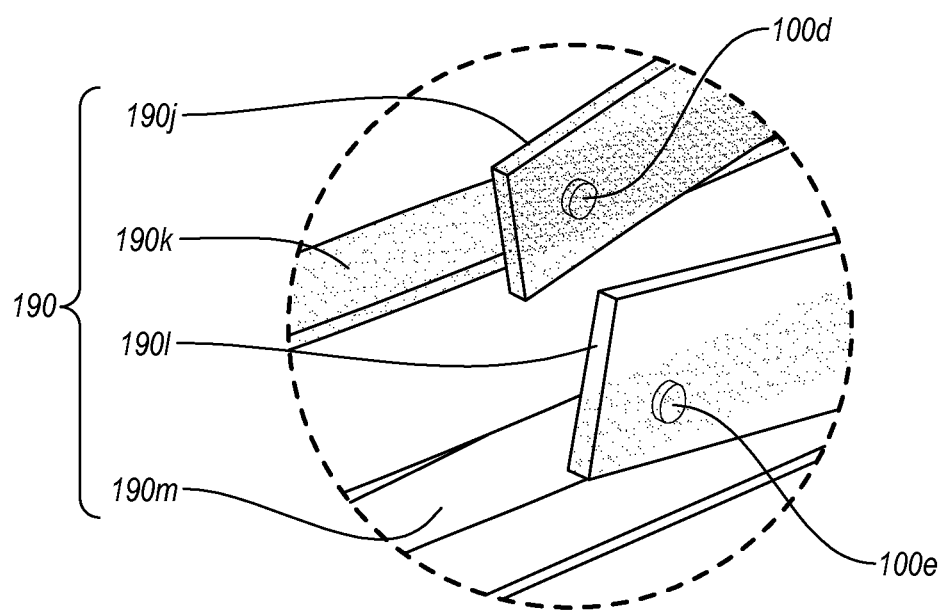
FIG. 10B illustrates an enlarged view of a portion of the resin-based lighting fixture of FIG. 10A.

One will appreciate in light of the disclosure herein that a manufacturer can vary the shape and configuration of the resin-based sculpture or lighting fixture by varying the shape, curvature, and/or number of resin pieces 190. For instance, FIGS. 10A-10B illustrate another implementation of a resin-based sculpture. In particular, FIGS. 10A-10B illustrate a basket-shaped lighting fixture 200b, which incorporates multiple resin pieces 190 secured together by resin-based fasteners. Except as otherwise described herein, the resin-based lighting fixture 200b and its components and elements can be similar to or the same as the resin-based lighting fixture 200a (FIGS. 9A-9B) and its respective components and elements.

In at least one implementation, the resin-based lighting fixture 200b can include resin pieces 190 that have different shades and/or colors. Moreover, the resin pieces 190 that form the basket shape of the resin-based lighting fixture 200b can overlap, thereby forming overlapping areas (described above) that also can have colors and/or shapes different from the individual resin pieces 190. As such, resin-based fasteners can secure together the overlapping resin pieces 190 and can blend in with the color and/or shade of the overlapping areas formed by the resin pieces 190.

For example, as illustrated in FIG. 10B, the resin-based rivet 100d can secure together first and second resin pieces 190j, 190k. The overlapping area formed by the resin pieces 190j, 190k can be darker (even when illuminated) than the shades of the individual resin pieces 190j, 190k. Accordingly, as noted above, the resin-based rivet 100d can match or blend in with the color and/or shade of the overlapping area formed by the resin pieces 190j, 190k.

In addition, in one or more implementations, the resin-based lighting fixture 200b can include third and fourth resin pieces 190l, 190m secured together by the resin-based rivet 100e. The resin pieces 190l, 190m can form an overlapping area that has a different shade and/or color than the individual resin pieces 190*l*, 190*m*. Consequently, similar to the resin-based rivet 100*d*, the resin-based rivet 100*e* can match the shade and/or color of the overlapping area formed by the resin pieces 190*l*, 190*m*, such that the resin-based rivet 100*e* blends in therewith.

Figure 11:
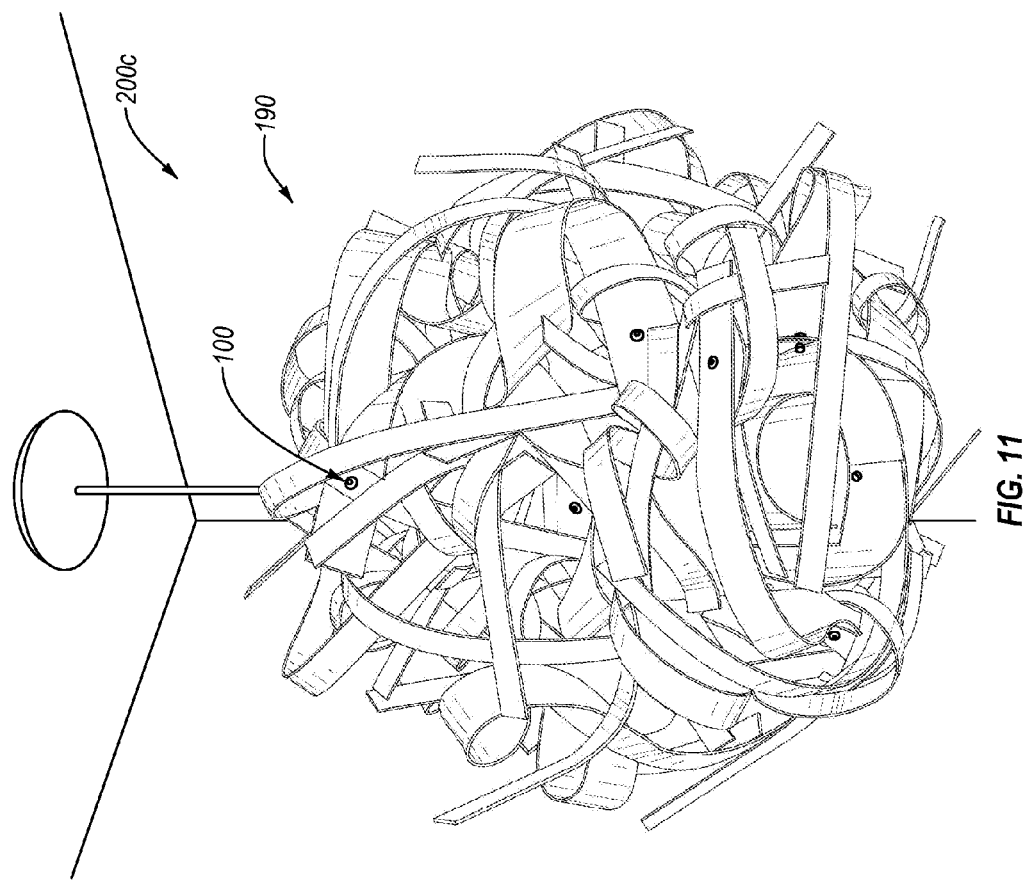
FIG. 11 illustrates a perspective view of a resin-based lighting fixture in accordance with yet another implementation of the present invention.

Implementations of the present invention also include resin-based sculptures or lighting fixtures that incorporate resin pieces 190, which overlap and or tangle together in other configuration. For example, FIG. 11 illustrates the resin-based lighting fixture 200*c* that includes multiple resin pieces 190 uniquely bent, shaped, and secured together with the resin-based rivets 100. Except as otherwise described herein, the resin-based lighting fixture 200*c* and its components and elements can be similar to or the same as the resin-based lighting fixtures 200*a*, 200*b* (FIGS. 9A-9B and 10A-10B) and their respective components and elements.

In particular, the resin-based lighting fixture 200*c* has multiple resin pieces 190 that have various ds twists, rolls, and/or otherwise irregular shapes. Additionally, the resin pieces 190 of the resin-based lighting fixture 200*c* can have any number of sizes, shapes, colors, textures, and transparent or translucent properties. When coupled together, however, the resin pieces 190 of the resin-based lighting fixture 200*c* can produce an approximately spherical shape of the resin-based lighting fixture 200*c*. In at least one implementation, the resin-based rivets 100 that couple such resin pieces 190 together can blend in with the resin pieces 190 in a manner that obscures or conceals connection points between the resin pieces 190. As such, the viewer can experience the aesthetic of the unique design of the resin-based lighting fixture 200*c*, undistracted by hardware components that fasten the resin pieces 190 together.

Figure 12:
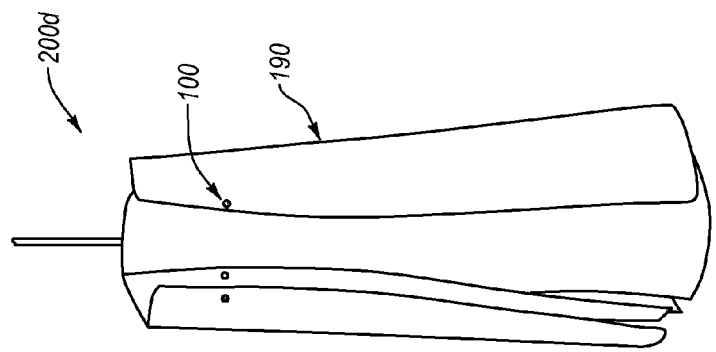
FIG. 12 illustrates a perspective view of a resin-based lighting fixture in accordance with one other implementation of the present invention.

The resin-based fasteners also can allow fabrication of resin-based sculptures or lighting fixtures that have fewer bends and/or larger exposed continuous surfaces. In light of this disclosure, it should be appreciated, however, that visible fasteners can be more noticeable and appear more intrusive on large exposed surfaces of the resin-based lighting fixtures and can, thus, detract from the aesthetic appeal thereof. Accordingly, implementations of the present invention include resin-based sculptures and lighting fixtures that comprise multiple resin pieces secured together by resin-based fasteners, which together form large exposed and visible surfaces. FIG. 12 illustrates one implementation of such a resin-based sculpture. Except as otherwise described herein, the resin-based lighting fixture 200*d* and its components and elements can be similar to or the same as the resin-based lighting fixture 200*a*, 200*b*, 200*c* (FIGS. 9A-9B, 10A-10B, and 11) and their respective components and elements.

More specifically, FIG. 12 illustrates the resin-based lighting fixture 200*d*, which includes multiple resin pieces 190 secured together by the resin-based rivets 100. The resin-based lighting fixture 200*d* also includes one or more large exposed surfaces formed by the resin pieces 190. As mentioned above, the resin-based rivets 100 can blend in with the resin pieces 190 and/or overlapping areas thereof, in a manner that resin-based rivets 100 can be largely invisible to the viewer. As such, the resin-based lighting fixture 200*d* can provide a pleasing aesthetic to the viewer. Moreover, the large exposed surfaces of the resin-based lighting fixture 200*d* also can emphasize the aesthetic of the resin pieces 190 incorporated therein.

Each of the resin-based sculptures or lighting fixtures shown and described herein above includes a pendant or hanging light configuration. One will appreciate in light of the disclosure herein that the present invention is not so limited. In alternative implementations, the resin-based lighting fixtures can comprise chandeliers, wall sconces, lamps, lights of ceiling fans, outdoor lighting, etc. One will appreciate that a manufacturer can design or configure a resin-based lighting fixture in almost limitless configurations using the principles of the present invention.

It should be also appreciated that the shapes and configurations described above are provided as examples. Generally, the ability to manipulate and shape the resin pieces as well as secure the resin pieces together with the resin-based fasteners can allow the manufacturer to create a wide variety of different shapes and configurations. Furthermore, implementations of the present invention are described herein primarily with reference to resin pieces, such as strips, panels, etc. One will also appreciate, however, that the strips, panels, etc., of the lighting fixtures of one or more implementations can include materials other than resin. For example, one or more strips of a given lighting fixture can include wood, stone, fiberglass, or the like.

Additionally, the resin pieces can comprise one or more layers of resin or other materials. For example, in one or more implementations, the resin pieces can include a decorative inter-layer, as explained in greater detail below. The decorative inter-layer can provide the resin-based sculptures with desirable aesthetic qualities. In addition to or in place of a decorative inter-layer, the resin pieces can be transparent, translucent, or opaque, depending upon the desired aesthetic. Furthermore, the resin pieces can include color, or can have a clear configuration.

The resin pieces can have a sheet gauge or thickness from as thin as about one-eighth inch (⅛") or one quarter inch (¼"), or thinner, to as thick as about one and one-half inches (1½") to about two inches (2"), or thicker, depending on the end-user's designs. In general, thicker gauges tend to be sturdier and more expensive than thinner gauges. In accordance with one or more implementations, the resin strips can have thinner gauges, such as anywhere from about one-sixteenth inch (1/16") to about three-eighths inch (⅜").

Figure 13:
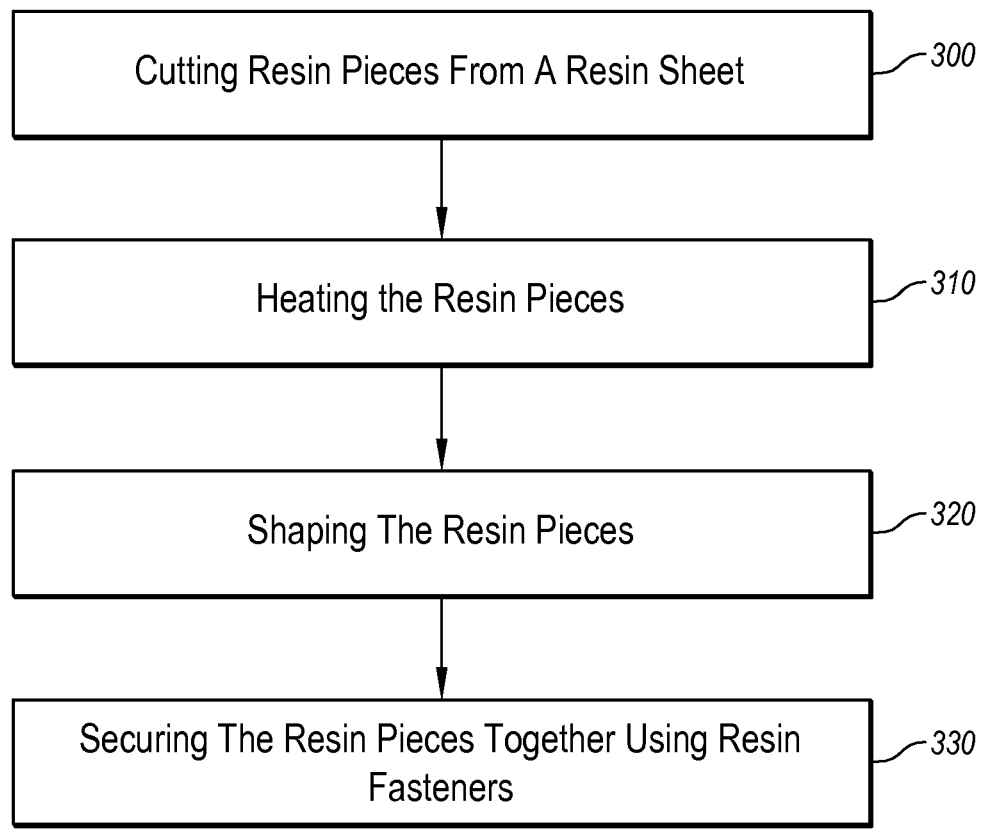
FIG. 13 illustrates a chart of acts of a method of forming a resin-based sculpture in accordance with one implementation of the present invention.

Accordingly, FIGS. 1-12 and the corresponding text, provide a number of different components and mechanisms for aesthetically pleasing resin-based lighting fixtures. In addition to the foregoing, implementations of the present invention can also be described in terms of flowcharts comprising acts and steps in a method for accomplishing a particular result. For example, FIG. 13 illustrates a flowchart of one exemplary method for manufacturing a resin-based sculpture or lighting fixture using principles of the present invention. The acts of FIG. 13 are described below with reference to the components and diagrams of FIGS. 1 through 12.

For example, FIG. 13 shows that a method of creating a resin-based sculpture, such as a resin-based lighting fixture 200*a*, 200*b*, 200*c*, 200*d* can comprise an act 300 of cutting resin strips or resin pieces 190 from a resin sheet. For example, the act 300 can involve cutting a plurality of resin pieces 190. Each of the resin pieces 190 can comprise any number thermoplastic materials described above Specifically, to form the resin pieces 190, a manufacturer can start with a resin sheet. The resin sheet can comprise any number of resin layers or decorative layers. For example, the resin sheet can include outer resin layers and an inner decorative layer. The decorative inter-layer can comprise fabric, metallic wire, rod and/or bar, papers, or photographic images. In yet additional implementations, the decorative inter-layer can comprise any organic, inorganic, naturally occurring, or synthetic materials such as rocks, crushed glass, minerals, leaves, twigs, branches, grasses, bamboo shoots, willow, thatch reed, solidified resins, metallic objects, vegetation, and so forth.

A manufacturer can choose the size and shapes of the resin pieces 190. The manufacturer can then lay out the shapes on a resin sheet. Moreover, the manufacturer can cut the resin pieces 190 out of the resin sheet. In some implementations, the manufacturer can perform these acts by hand. In additional or alternative implementations, the manufacturer can at least partially automate cutting of the resin pieces 190, such as by using a CNC (computer numerically controlled) machine. The CNC machine also can help to maximize the number of resin pieces 190 cut from each resin sheet. In yet further implementations, the resin pieces 190 can comprise, or be cut from, resin scraps from other projects.

The resin sheets from which a manufacturer can cut the resin pieces 190 can comprise any of the thermoplastic materials described herein above. Furthermore, the resin sheets may have a thickness or gauge of about two inches (2"), about one inch (1"), about one-half inch (½"), about one-fourth inch (¼"), about one-eighth inch (⅛"), about one-sixteenth inch (1/16"), or about one-thirty-second inch (1/32").

In addition, FIG. 13 shows that the method can comprise an act 310 of heating the resin pieces 190. Act 310 can include heating the resin pieces 190 to a processing temperature approximately equal to the glass transition temperature of the resin material(s) of the resin pieces 190. For example, a manufacturer can heat the resin pieces 190 in an oven. Alternatively or additionally, the manufacturer can heat the resin pieces 190 in a lamination press, autoclave, vacuum bag, or other thermosetting environment.

Generally, the manufacturer can heat the resin pieces 190 until they are pliable. One will appreciate that the temperatures to which the manufacturer heats the resin pieces 190 can depend upon the particular resins used to form the resin pieces 190. For example, in implementations in which copolyester (e.g., PETG) is used, the manufacturer can place the resin pieces 190 in an oven preheated to a temperature of about 350° F. for about one minute. In alternative implementations, the manufacturer can heat the resin pieces 190 to a temperature of between about 180° F. and about 275° F., such as to a temperature of about 225° F. In any event, the manufacturer can heat the resin pieces 190 to a temperature near or above their glass transition temperature.

FIG. 13 also shows that the method comprises an act 320 of shaping the resin pieces 190. Act 320 can include shaping one or more of the resin pieces 190, only some of the resin pieces 190, or all of the resin pieces 190. The method also can include shaping the resin pieces 190 using a mold or other mechanism or device.

The act 320 can further involve providing each of the resin pieces 190 with a unique or the same curvature as the other resin pieces 190. During the shaping operation, the manufacturer can impart curvature or other non-linear geometry to one or more resin pieces 190. For example, the manufacturer can provide each resin piece 190 with varying degrees of curvature or shape.

In one or more implementations, the manufacturer can shape the resin pieces 190 by hand. One will appreciate in light of the disclosure herein that shaping the resin pieces 190 by hand can provide each of the resin pieces 190 with a unique configuration. Accordingly, any one of the resin-based lighting fixtures 200a, 200b, 200c, 200d also can have a unique shape and/or configuration. In alternative implementations, the manufacture can shape the resin pieces 190 by pressing the resin pieces 190 against or between mold(s).

In any event, the manufacturer can provide one or more of the resin pieces 190 with curvature or other non-planar geometry.

In addition to the foregoing, the method can comprise an act 330 of assembling the resin pieces 190 about a mounting fixture, such as the mounting fixture 220a. In particular, the act 330 can involve securing the resin pieces 190 together with one or more resin-based fasteners. For instance the manufacturer can secure together the resin pieces 190 with the resin-based rivets 100, 100a, 100d, 100e. In additional or alternative implementations, the manufacturer can secure the resin pieces 190 together with the resin-based screws 100b and/or with the resin-based clips 100c.

Additionally, the act 330 can involve assembling the resin pieces 190 about the mounting fixture (e.g., about the mounting fixture 220a). In one implementation, the manufacturer can incorporate one or more light sources 230, which can illuminate the resin-based lighting fixture 200a, 200b, 200c, 200d as well as the resin pieces 190 thereof. The act 330 also can involve arranging the one or more resin pieces 190 into a blossom or flower configuration.

Furthermore, the manufacturer can modify the color and opacity/translucence of the resin pieces 190 or of the resin-based fasteners (i.e., resin-based rivets 100, 100a, 100d, 100e, resin-based screws 100b, and/or resin-based clips 100c) in any number of ways to adjust the opacity/transparency of the resin-based lighting fixture for desired aesthetic effect. In at least one implementation, the manufacturer can modify the hue, color intensity, and light transmission of the resin pieces 190 and/or the decorative inter-layer to vary the resultant aesthetic properties of the resin-based lighting fixture. Accordingly, one or more implementations of the present invention provide a manufacturer with a number of ways to prepare an aesthetically desirable resin-based lighting fixture. These resin-based lighting fixtures can have a wide range of shapes, sizes, thicknesses, properties or colors, and can be used in a wide range of environments and applications.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

I claim:

1. A resin-based sculpture, comprising:
   a plurality of resin strips; and
   one or more resin-based fasteners securing the plurality of resin strips together, each of the resin-based fasteners having a mandrel and a main body, wherein the mandrel is movable relative to the main body, such that, upon insertion through an opening in the head of the main body, the main body is split, on at least one end, into a plurality of legs that thereby secure the one or more resin-based fasteners to the plurality of resin strips;
   wherein:
   one or more resin strips of the plurality of resin strips are shaped to form a decorative design, and
   a color and resin material of the one or more resin-based fasteners matches a color and resin material of the one or more resin strips of the plurality of resin strips which are secured by the one or more resin-based fasteners.

2. The resin-based sculpture as recited in claim 1, wherein a shade of the one or more resin-based fasteners is darker than a shade of the one or more resin strips which are secured by the one or more resin-based fasteners.

3. The resin-based sculpture as recited in claim 1, wherein the one or more resin-based fasteners are transparent.

4. The resin-based sculpture as recited in claim 1, wherein the one or more resin-based fasteners comprise rivets.

5. The resin-based sculpture as recited in claim 1, wherein the one or more resin-based fasteners comprise clips or screws.

6. The resin-based sculpture as recited in claim 1, wherein a first resin strip includes a different curvature than at least a second resin strip.

7. The resin-based sculpture as recited in claim 6, wherein each resin strip of the plurality of resin strips includes a different curvature.

8. The resin-based sculpture as recited in claim 1, further comprising one or more decorative layers positioned within one or more of the resin strips.

9. The resin-based sculpture as recited in claim 8, wherein the one or more decorative layers comprise a fabric layer.

10. The resin-based sculpture as recited in claim 1, wherein:
   each resin strip has a gauge of between about ⅛ an inch and about ¼ an inch; and
   each resin strip comprises PETG.

11. The resin-based sculpture as recited in claim 1, further comprising:
   one or more slots formed about the plurality of legs on each fastener;
   wherein the one or more slots facilitate light transmission through each fastener.

12. The resin-based sculpture as recited in claim 11, wherein:
   the head comprises a main body opening into which the mandrel is advanced, and a countersink opening that fits a top portion of the mandrel; and
   the top portion of the mandrel is wider than the opening into which the mandrel is advanced.

13. The resin-based sculpture as recited in claim 12, wherein the main body opening into which the mandrel is advanced is conical.

14. The resin-based sculpture as recited in claim 1, wherein each main body comprises:
   a head; and
   a blind end that comprises the plurality of legs.

15. A resin-based lighting fixture, comprising:
   a plurality of resin pieces; and
   a plurality of resin-based rivets securing the plurality of resin pieces together, each of the resin-based rivets having a mandrel and a main body, wherein the mandrel is movable relative to the main body, such that, upon insertion through an opening in the head of the main body, the main body is split, on at least one end, into a plurality of legs that thereby secure the plurality of resin-based rivets and the plurality of resin pieces together; and
   a lighting source at least partially surrounded by the plurality of resin pieces,
   wherein:
   one or more resin pieces of the plurality of resin pieces are shaped to form a decorative design, and
   a color, transparency, and resin material of the plurality of resin-based rivets matches a color, transparency, and resin material of the plurality of resin pieces, such that the plurality of resin-based rivets blends with the secured plurality of resin pieces.

16. The resin-based sculpture as recited in claim 15, further comprising a mounting fixture supporting the plurality of resin strips.

17. The resin-based sculpture as recited in claim 16, wherein the mounting fixture comprises a light socket.

18. The resin-based sculpture as recited in claim 15, wherein a shade of the one or more resin-based rivets is lighter than a shade of the one or more resin strips which are secured by the one or more resin-based rivets.

19. The resin-based sculpture as recited in claim 15, wherein a first resin piece includes a different curvature than at least a second resin piece.

20. The resin-based sculpture as recited in claim 19, wherein each resin strip piece of the plurality of resin strips pieces includes a different curvature.

21. The resin-based sculpture as recited in claim 15, further comprising:
   one or more slots formed about the plurality of legs on each fastener;
   wherein the one or more slots facilitate light transmission through each fastener.

22. The resin-based lighting fixture as recited in claim 15, wherein each main body comprises:
   a head; and
   a blind end that comprises the plurality of legs.

23. The resin-based lighting fixture as recited in claim 22, wherein:
   the head comprises a main body opening into which the mandrel is advanced, and a countersink opening that fits a top portion of the mandrel; and
   the top portion of the mandrel is wider than the opening into which the mandrel is advanced.

24. The resin-based sculpture as recited in claim 23, wherein the main body opening into which the mandrel is advanced is conical.

25. A method of forming a resin-based sculpture, comprising:
   cutting a plurality of resin pieces from a resin sheet made of a resin material having a texture;
   heating the resin pieces;
   shaping two or more resin pieces of the plurality of resin pieces;
   securing a first resin piece of the two or more resin pieces to a second resin piece of the two or more resin pieces using a resin-based fastener having a color that matches a color of one or more of the first and second resin pieces, the resin-based fastener having a mandrel and a main body, wherein the mandrel is movable relative to the main body such that, inserting the mandrel within the main body causes the main body, on at least one end, to split into a plurality of legs that secure the mandrel to the main body of the fastener; and
   assembling the resin strips about a mounting fixture.

26. The method as recited in claim 25, further comprising dying the resin-based fastener to match the two or more resin strips.

27. The method as recited in claim 25, wherein heating the resin strips comprises heating the resin strips to a temperature approximately equal to a glass transition temperature of the resin strips.

28. The method as recited in claim 25, wherein the resin-based fastener is a lighter shade of the color than a shade of the first and second resin strips.

29. The method as recited in claim 25, further comprising inserting the mandrel within each main body so that the mandrel is flush with a head of the main body.

30. The method as recited in claim 29, wherein:
the main body comprises head portion having a countersink shape; and
the mandrel comprises a countersinking top portion that is thicker than the mandrel, the countersinking top portion shaped to fit reciprocally within the countersink shape of the head of the main body so that the mandrel top portion is flush with the head portion when the plurality of legs is split.

31. The method as recited in claim 29, further comprising:
selecting for the resin-based fastener a resin material having a texture, so that the resin material and texture of the resin-based fastener matches the resin material and texture of the resin sheet.

\* \* \* \* \*